(12) United States Patent
Bode et al.

(10) Patent No.: US 12,714,361 B2
(45) Date of Patent: Aug. 25, 2026

(54) MEDICAL DEVICES AND METHODS FOR ADMINISTERING BASAL INSULIN DOSE AND BOLUS INSULIN DOSE

(71) Applicant: Sanofi, Paris (FR)

(72) Inventors: Andreas Bode, Frankfurt Am Main (DE); Jochen Sieber, Frankfurt (DE); Lars Krinelke, Edinburgh (GB)

(73) Assignee: Sanofi, Paris (FR)

( * ) Notice: Subject to any disclaimer, the term of this patent is extended or adjusted under 35 U.S.C. 154(b) by 1149 days.

(21) Appl. No.: 17/616,612

(22) PCT Filed: Jun. 2, 2020

(86) PCT No.: PCT/EP2020/065152
§ 371 (c)(1),
(2) Date: Dec. 3, 2021

(87) PCT Pub. No.: WO2020/245090
PCT Pub. Date: Dec. 10, 2020

(65) Prior Publication Data

US 2022/0225931 A1 Jul. 21, 2022

(30) Foreign Application Priority Data

Jun. 5, 2019 (EP) ..................................... 19305725

(51) Int. Cl.
*A61B 5/00* (2006.01)
*A61B 5/145* (2006.01)
(Continued)

(52) U.S. Cl.
CPC ........ *A61B 5/4839* (2013.01); *A61B 5/14532* (2013.01); *A61M 5/14244* (2013.01);
(Continued)

(58) Field of Classification Search
CPC ............. A61B 5/4839; A61B 5/14532; A61M 5/14244; A61M 5/1723;
(Continued)

(56) References Cited

U.S. PATENT DOCUMENTS 6,827,702 B2 12/2004 Ebel et al.
6,852,104 B2 2/2005 Blomquist
(Continued)

FOREIGN PATENT DOCUMENTS

CN 103083756 A 5/2013
CN 106687964 A 5/2017
(Continued)

OTHER PUBLICATIONS

International Preliminary Report on Patentability, PCT/EP2020/065152 (Dec. 12, 2021).
(Continued)

*Primary Examiner* — Bhisma Mehta
*Assistant Examiner* — Fatimata Sahra Diop
(74) *Attorney, Agent, or Firm* — McCarter & English, LLP

(57) ABSTRACT

A medical device and method for determining a basal dose of insulin and a bolus dose of insulin to be administered for glycemic control is provided. The medical device includes an insulin pump, a control interface including a button configured to select one of a plurality of present bolus insulin doses based on input from a user (e.g., a patient), and a controller configured for executing instructions to determine a basal insulin delivery rate based, at least in part, on a total daily basal insulin dose and to determine the plurality of preset bolus insulin doses based, at least in part, on a total daily bolus insulin dose.

20 Claims, 5 Drawing Sheets

300

Determine total daily basil insulin dose and total daily bolus insulin dose for user based on dosing information for user received via input interface of control unit of medical device
302

Determine plurality of preset bolus insulin doses for selection based, at least in part, on total daily insulin dose, total daily basal insulin dose, or total daily bolus insulin dose for user
304

Determine basal insulin delivery rate based on total basal insulin dose
306

Actuate insulin pump to deliver insulin to user at basal insulin delivery rate
308

Receive first input from user via button of control interface selecting one of plurality of preset bolus insulin doses
310

Provide indication of selected present bolus insulin dose
311

Receive second input from user via control interface confirming selected preset bolus insulin dose
312

Actuate insulin pump of pump unit to deliver selected preset insulin dose to user
314

(51) Int. Cl.
*A61M 5/142* (2006.01)
*A61M 5/172* (2006.01)
*G16H 20/17* (2018.01)

(52) U.S. Cl.
CPC .......... *A61M 5/1723* (2013.01); *G16H 20/17* (2018.01); *A61M 2005/14208* (2013.01); *A61M 2205/3327* (2013.01); *A61M 2205/502* (2013.01)

(58) Field of Classification Search
CPC ........... A61M 2005/14208; A61M 2205/3327; A61M 2205/502; A61M 5/142; A61M 5/172; G16H 20/17
See application file for complete search history.

(56) References Cited

U.S. PATENT DOCUMENTS 7,806,886 B2 10/2010 Kanderian, Jr. et al.
7,815,602 B2 10/2010 Mann et al.
7,850,641 B2 12/2010 Lebel et al.
8,348,923 B2 1/2013 Kanderian, Jr. et al.
8,690,856 B2 4/2014 Blomquist
8,777,924 B2 7/2014 Kanderian, Jr. et al.
8,801,657 B2 8/2014 Blomquist et al.
8,845,613 B2 9/2014 Yodfat et al.
9,173,991 B2 11/2015 Yodfat et al.
9,326,709 B2 5/2016 Budiman
9,446,186 B2 9/2016 Estes
9,757,510 B2 9/2017 Finan
2003/0212364 A1 11/2003 Mann et al.
2003/0212379 A1 11/2003 Bylund et al.
2008/0234663 A1 9/2008 Yodfat et al.
2009/0036753 A1 2/2009 King
2013/0245547 A1 9/2013 El-Khatib et al.
2015/0366945 A1 12/2015 Greene
2017/0021100 A1 1/2017 Starkweather et al.
2017/0049960 A1 2/2017 Nguyen
2017/0203037 A1* 7/2017 Desborough ........ A61B 5/4839
2017/0203038 A1 7/2017 Desborough et al.
2017/0232195 A1* 8/2017 Desborough .......... G16H 20/17 604/504
2017/0351842 A1 12/2017 Booth et al.
2018/0085532 A1 3/2018 Desborough et al.
2018/0089395 A1 3/2018 Desborough et al.
2018/0133398 A1* 5/2018 Blomquist .......... A61M 5/1723
2018/0200436 A1* 7/2018 Mazlish ................. G16H 50/30
2018/0296757 A1 10/2018 Finan et al.

FOREIGN PATENT DOCUMENTS

CN 107135644 A 9/2017
JP 2010-534494 A 11/2010
WO 2003022327 A2 3/2003
WO 2008088490 A1 7/2008
WO 2009/002622 A2 12/2008
WO 2011/117270 A1 9/2011
WO 2016/048823 A1 3/2016
WO 2018/033513 A1 2/2018
WO 2018033514 A1 2/2018
WO 2018/194838 A1 10/2018

OTHER PUBLICATIONS

International Search Report, PCT/EP2020/065152 (Jul. 21, 2020).
Zisser, Howard, et al. "Bolus calculator: a review of four 'smart' insulin pumps," Diabetes Technol. & Therapeutics, 10(6):441-4 (Dec. 2008).
Chinese Office Action for Application No. 202080054197.0, dated Nov. 27, 2024, 11 pages.

* cited by examiner

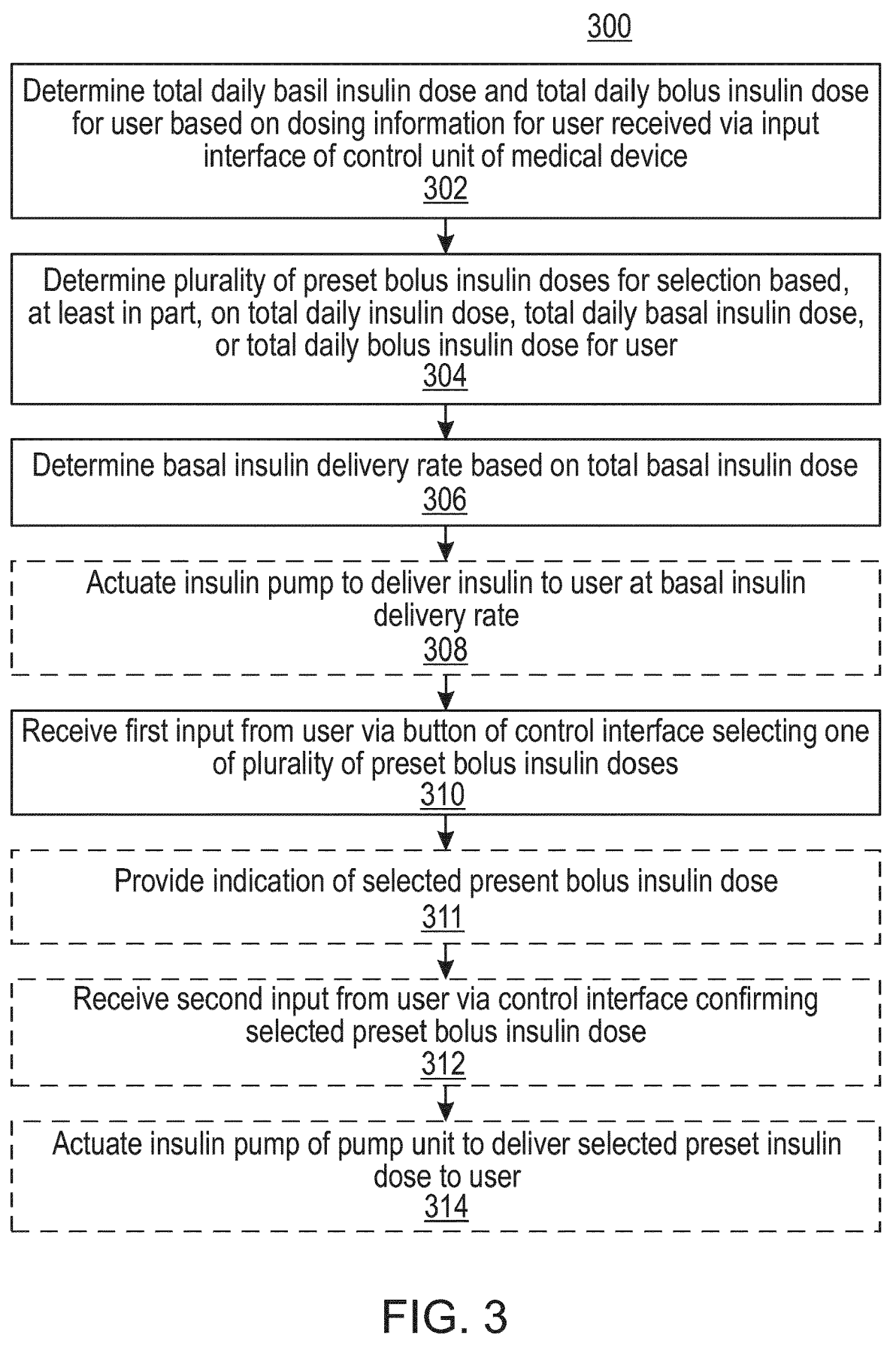

300

Determine total daily basil insulin dose and total daily bolus insulin dose for user based on dosing information for user received via input interface of control unit of medical device
302

Determine plurality of preset bolus insulin doses for selection based, at least in part, on total daily insulin dose, total daily basal insulin dose, or total daily bolus insulin dose for user
304

Determine basal insulin delivery rate based on total basal insulin dose
306

Actuate insulin pump to deliver insulin to user at basal insulin delivery rate
308

Receive first input from user via button of control interface selecting one of plurality of preset bolus insulin doses
310

Provide indication of selected present bolus insulin dose
311

Receive second input from user via control interface confirming selected preset bolus insulin dose
312

Actuate insulin pump of pump unit to deliver selected preset insulin dose to user
314

FIG. 3

MEDICAL DEVICES AND METHODS FOR ADMINISTERING BASAL INSULIN DOSE AND BOLUS INSULIN DOSE

RELATED APPLICATION

The present application is a 35 U.S.C. § 371 national stage filing of International Application No. PCT/EP2020/065152, filed on Jun. 2, 2020, which in turn claims the benefit of and priority to European Application No. 19305725.4, filed Jun. 5, 2019. The entire contents of each of the aforementioned applications are incorporated by reference herein in their entirety.

FIELD OF THE INVENTION

The present invention relates to a medical device and a method for administering a basal dose of insulin and a bolus dose of insulin.

BACKGROUND

People with diabetes are either deficient in insulin or cannot make sufficient insulin to overcome underlying insulin resistance or to normalize the glucose metabolism. Basal insulin or insulin glargine treatment is often used to achieve improved glycemic control. Although blood glucose levels fluctuate throughout the day, "perfect glycemic control" would mean that glucose levels are always in a range of 70 to 130 mg/dl or 3.9 to 7.2 mmol/L and indistinguishable from a person without diabetes. Basal insulin or insulin glargine therapy combined with a bolus insulin dosage can be used achieve improved glycemic control or to get as close as possible to "perfect glycemic control". In this therapy, basal insulin is provided throughout the day which is supplemented using a bolus insulin dosage (e.g., based on the characterization of a meal). However, finding the correct bolus dose for a meal is complex. An accurate bolus dose depends on carbohydrate "carb" counting, an insulin to carb ratio, and a glucose correction factor. Because of these difficulties in determining an accurate bolus insulin dosage, patients are less likely to employ mealtime bolus doses.

Further, the complexity and difficulty in programming a bolus dosage in some conventional insulin pumps further decreases the likelihood of patients employing mealtime boluses in their treatment. For example, for some conventional insulin pumps, programming the pump to deliver a bolus insulin dosage requires starting from zero to the desired bolus insulin dosage. In some conventional insulin pumps, programming the insulin pump used in basal insulin therapy to administer a bolus insulin dosage requires multistep programming and/or is time-consuming. Additionally, manually programming a pump to administer a bolus insulin dosage may result in inadvertent errors in dosage. For example, the wrong dosage may be entered.

SUMMARY

Some exemplary embodiments of the present disclosure are directed to a medical device for administering daily basal insulin to a user of the medical device (e.g., a patient) and enabling easy and simple user selection of one of a plurality of preset bolus insulin doses, which are based on a determined total daily bolus insulin dose. A total daily insulin dose and the determined total daily bolus insulin dose are based on received dosing information for the user, e.g., information received from a health care provider. In some embodiments, the plurality of predetermined bolus insulin doses correspond to doses required for meals with different amounts of carbohydrates, and to smaller correction doses. In some embodiments, user selection of one of the predetermined bolus insulin doses is via a button of the medical device. In some embodiments, user selection of one of the preset bolus insulin doses is based on a number of times that the user pushes the button. In some embodiments, the medical device is configured to provide information regarding the selected preset bolus insulin doses, e.g., via a vibration of the medical device or a sound made by the medical device. In some embodiments, the medical device is configured to receive an input from the user confirming the selected preset bolus insulin dose. In some embodiments, the input confirming the selected preset bolus insulin dose is via a second button of the medical device. In some embodiments, the medical device does not include a graphical user interface. In some embodiments, the control interface of the medical device does not include a screen or a display.

Some embodiments provide a medical device that enables simple selection of a bolus insulin dose to increase compliance with a bolus insulin therapy.

Some embodiments may improve glycemic control by providing a medical device that enables easy characterization of a meal instead of complex carbohydrate counting and complex calculations for selection of a preset bolus insulin dosage.

Some embodiments may increase adoption of bolus insulin therapy by making it easier for the health care provider (HCP) to program the pump for bolus insulin dose therapy.

Some embodiments are directed to a medical device that includes an insulin pump configured to deliver insulin, a control interface including a button configured to select one of a plurality of preset bolus insulin doses based on an input from a user, and a controller configured for executing instructions stored in a memory. In some embodiments, the controller is configured to execute instructions stored in a memory to determine a total daily basal insulin dose and a total daily bolus insulin dose for the user based on information received. In some embodiments, the information received is information regarding at least two of the following: (i) a total daily insulin dose for the user, (ii) a total daily basal insulin dose for the user, (iii) a total daily bolus insulin dose for the user, and (iv) a ratio of a total daily basal insulin dose to a total daily bolus insulin dose for the user. In some embodiments, the medical device is configured based on the assumption that the total daily basal insulin dose is the same as the total daily bolus insulin dose, in which case, the information received may include only one or more of the following: (i) a total daily insulin dose for the user, (ii) a total daily basal insulin dose for the user, and (iii) a total daily bolus insulin dose for the user.

The controller is configured to execute instructions stored in a memory to determine the plurality of preset bolus insulin doses based, at least in part, on the total daily bolus insulin dose, and to determine a basal insulin delivery rate based, at least in part, on the total daily basal insulin dose. The executed instructions further cause delivery of insulin, via the insulin pump, to the user at the basal insulin delivery rate. The controller is configured to execute instructions stored in a memory to receive a first input from the user via the button selecting one of the plurality of preset bolus insulin doses, and to deliver the selected bolus insulin dose, via the insulin pump, to the user.

In some embodiments, execution of the instructions further causes the controller to determine a count of the button activations by the user during a selection time period, where the selection time period starts when the button is first activated, and, based on the count of the button activations by the user during the selection time period, select one of the plurality of preset bolus insulin doses.

In some embodiments, the medical device is configured to select a preset bolus insulin dose amongst the plurality of preset bolus insulin doses based on the count of the button activations by the user during the selection time period. In some embodiments, an increase in the count of the button activations by the user during the selection time period results in selection of a preset bolus insulin dose with a progressively larger quantity of insulin.

In some embodiments, execution of the instructions further causes the controller to provide information indicating the selected preset bolus insulin dose to the user via the control interface. In some embodiments, the information indicating the selected preset bolus insulin dose is provided, at least in part, in the form of a vibration or movement generated via the control interface. In some embodiments, the information indicating the selected preset bolus insulin dose is provided, at least in part, in the form of sound generated via the control interface. In some embodiments, the information indicating the selected preset bolus insulin dose in provided via a visual indication.

In some embodiments, the medical device may receive a second input from the user via the control interface confirming the selected preset bolus insulin dose within a confirmation time period after selection of the preset bolus insulin dose. For example, in some embodiments, the medical device may provide information indicating the selected preset bolus insulin dose, and the user may confirm the selected preset bolus insulin dose in response to or after receiving the provided information. In some embodiments, the control interface further comprises a second button configured to confirm the selection of the preset bolus insulin dose and the user confirms the selected preset bolus insulin dose by pressing or touching the second button. In some other embodiments, the second input for confirmation of the selected preset bolus insulin dose may be received via the button used for initially making the selection of the preset bolus insulin dose.

In some embodiments, the user does not need to provide any input or information regarding calories, carbohydrates, glycemic index, or a blood glucose level prior to selection of the preset bolus insulin dose.

In some embodiments, the doses in the plurality of preset bolus insulin doses are determined as fractions of the total daily bolus insulin dose.

In some embodiments, the preset bolus insulin doses in the plurality of bolus insulin doses are not linearly increasing.

In some embodiments, the plurality of preset bolus insulin doses includes a set of main preset bolus insulin doses and a set of correction preset bolus insulin doses, where each correction preset bolus insulin dose is smaller than all of the main preset insulin doses. In some embodiments, a spacing between two preset bolus insulin doses in the set of correction preset bolus insulin doses is smaller than a spacing between any two of the preset bolus insulin doses in the set of main preset bolus insulin doses. In some embodiments, the main preset bolus insulin doses correspond to meals having various amounts of carbohydrates.

In some embodiments, the plurality of preset bolus insulin doses are not determined based, at least in part, on the preset daily insulin bolus dose, but are instead determined based, at least in part, on the total daily insulin dose or on the total daily basal insulin dose.

In some embodiments, execution of the instructions causes the controller to determine micro-bolus insulin doses and a frequency for administration of the micro-bolus insulin doses to the user to achieve the determined basal insulin delivery rate, and to deliver to the user, via the insulin pump, the determined micro-bolus insulin doses at the determined frequency.

In some embodiments, execution of the instructions causes the controller to receive, via an input interface, information regarding insulin dosing for the user from which the total daily basal insulin dose and the total daily bolus insulin dose for the user are determined, and to store the received information in the memory.

In some embodiments, the medical device includes a control unit that includes the controller and the control interface, and a pump unit that includes the insulin pump. In some embodiments, the medical device also includes a blood glucose measuring unit configured to determine a blood glucose value that corresponds to a current blood glucose level of the user.

Some embodiments provide a control unit for a medical device. The control unit includes a control interface including a button configured to select one of a plurality of preset bolus insulin doses based on an input from a user. The control unit also includes a controller configured for executing instructions stored in a memory. The controller executes instructions to determine a total daily basal insulin dose and a total daily bolus insulin dose for the user based on information received regarding the user. In some embodiments, the information received includes information regarding at least two of: i) a total daily insulin dose for the user, ii) a total daily basal insulin dose for the user, iii) a total daily bolus insulin dose for the user, and iv) a ratio of the total daily basal insulin dose to the total daily bolus insulin dose for the user. In some embodiments, the information received includes information regarding one or more of: i) a total daily insulin dose for the user, ii) a total daily basal insulin dose for the user, iii) a total daily bolus insulin dose for the user and it is assumed that the total daily basal insulin dose is the same as the total daily bolus insulin dose. The instructions executed by the controller further cause the controller to determine the plurality of preset bolus insulin doses based, at least in part, on the total daily bolus insulin dose, and to determine a basal insulin delivery rate based, at least in part, on the total daily basal insulin dose. The instructions executed by the controller further cause the controller to actuate, via a drive unit, the insulin pump of the pump unit to deliver insulin, via the insulin pump, to the user at the basal insulin delivery rate. In some embodiments, the drive unit is included in the control unit. In some embodiments, the drive unit is included in the pump unit. In some embodiments, the drive unit is not included in the control unit or in the pump unit. The instructions executed by the controller further cause the controller to receive a first input from the user via the button selecting one of the plurality of preset bolus insulin doses, and to actuate, via the drive unit, the insulin pump of the pump unit to deliver the selected bolus insulin dose to the user.

In some embodiments, the control unit is configured to determine a count of the button activations by the user during a selection time period, where the selection time period starts when the button is first activated, and, based on the count of the button activations by the user during the selection time period, select one of the plurality of preset bolus insulin doses.

In some embodiments, the control unit selects a preset bolus insulin dose amongst the plurality of preset bolus insulin doses based on the count of the button activations by the user during the selection time period where an increase in the count of the button activations by the user during the selection time period results in selection of a preset bolus insulin dose with a progressively larger quantity of insulin.

Some embodiments provide a method for determining a total daily basal insulin dose and a total daily bolus insulin dose for a user based on information received, via an input interface of a medical device, regarding at least two of a total daily insulin dose for the user, a total daily basal insulin dose for the user, a total daily bolus insulin dose for the user, and a ratio of a total daily basal insulin dose to a total daily bolus insulin dose for the user. The method can include determining, via the controller of the medical device, a plurality of preset bolus insulin doses for selection using a button of a control interface of the medical device based, at least in part, on the total daily bolus insulin dose for the user. The method can include determining via the controller of the control unit, a basal insulin delivery rate based, at least in part, on the total daily basal insulin dose. The method can include receiving a first input from the user via the button of the control interface of the control unit, the first input selecting one of the plurality of preset bolus insulin doses. In some embodiments, the method also includes providing information indicating the selected preset bolus insulin dose to the user via the control interface. In some embodiments, the method can include receiving a second input from the user via the control interface confirming the selected preset bolus insulin dose within a confirmation time period after selection of the preset bolus insulin dose. In some embodiments the method further includes actuating, via a drive unit of the medical device, an insulin pump of the medical device to deliver insulin, via the insulin pump to the user at the basal insulin delivery rate. In some embodiments, the method further includes actuating, via the drive unit, the insulin pump to deliver the selected bolus insulin dose to the user.

Some embodiments provide a method for determining and administering basal insulin and bolus insulin doses to a user using any of the medical devices described herein.

Some embodiments provide a method for determining and administering basal insulin and bolus insulin doses to a user. The method includes determining, by a controller of a medical device, a total daily basal insulin dose and a total daily bolus insulin dose for a user based on information received regarding dosing for the user, via an input interface of the medical device. In some embodiments, the received information regarding dosing for the user includes information regarding at least two of: i) a total daily insulin dose for the user, ii) a total daily basal insulin dose for the user, iii) a total daily bolus insulin dose for the user, and iv) a ratio of the total daily basal insulin dose to the total daily bolus insulin dose for the user. In some embodiments, the received information regarding dosing for the user includes information regarding one or more of: i) the total daily insulin dose for the user, ii) the total daily basal insulin dose for the user, and iii) the total daily bolus insulin dose for the user, and the method assumes that the total daily basal insulin dose is the same as the total daily bolus insulin dose. The method also includes determining, by the controller, a plurality of preset bolus insulin doses for selection using a button of a control interface of the medical device based, at least in part, on the total daily bolus insulin dose for the user. The method also includes determining, by the controller, a basal insulin delivery rate based, at least in part, on the total daily basal insulin dose. The method also includes delivering insulin to the user at the basal insulin delivery rate using an insulin pump of the medical device. The method also includes receiving a first input from the user via a button of the control interface of the medical device, the first input selecting one of the plurality of preset bolus insulin doses. In some embodiments the method also includes providing information indicating the selected preset bolus insulin dose to the user via the control interface. In some embodiments, the information indicating the selected preset bolus insulin dose is provided by one or more of vibration of the medical device, a sound emitting by the medical device, or a visual indication. In some embodiments, method also includes receiving a second input from the user via the control interface confirming the selected preset bolus insulin dose within a confirmation time period after selection of the preset bolus insulin dose. The method includes delivering the preset bolus insulin dose to the user via the infusion pump. In embodiments that include receiving a second input via the control interface confirming the selected preset bolus insulin dose prior to delivery of the preset bolus insulin dose, the selected preset bolus insulin dose is a confirmed preset bolus insulin dose.

Some embodiments provide a method for determining a basal insulin delivery rate and a bolus insulin dose for a user. The method includes determining a total daily basal insulin dose and a total daily bolus insulin dose for a user based on dosing information for the user received via an input interface of a control unit. In some embodiments, the control unit is a reusable control unit. In some embodiments, the dosing information includes information regarding at least two of: i) a total daily insulin dose for the user, ii) a total daily basal insulin dose for the user, iii) a total daily bolus insulin dose for the user, and a iv) ratio of the total daily basal insulin dose to the total daily bolus insulin dose for the user. In some embodiments, the dosing information includes information regarding one or more of: i) the total daily insulin dose for the user, ii) the total daily basal insulin dose for the user, iii) the total daily bolus insulin dose for the user, where the method assumes that the total daily bolus insulin dose for the user and the total daily basal insulin dose for the user are the same. The method includes determining, via the controller of the control unit, a plurality of preset bolus insulin doses for selection using a button of a control interface of the control unit, based, at least in part, on the total daily bolus insulin dose for the user. The method includes determining via a controller of the control unit, the basal insulin delivery rate based, at least in part, on the total daily basal insulin dose. The method includes receiving a first input from the user via the button of the control interface of the control unit, the first input selecting one of the plurality of preset bolus insulin doses. In some embodiments, the method includes providing information indicating the selected preset bolus insulin dose to the user via the control interface. In some embodiments, the method can include receiving a second input from the user via the control interface confirming the selected preset bolus insulin dose within a confirmation time period after selection of the preset bolus insulin dose. In some embodiments, the method further includes actuating, via the drive unit, the insulin pump to deliver the selected bolus insulin dose, via the insulin pump to the user.

In embodiments that include receiving a second input via the control interface confirming the selected preset bolus insulin dose prior to transferring the second information, the selected preset bolus insulin dose is a confirmed preset bolus insulin dose. In some embodiments, in which the insulin pump is actuated, the method is a method of delivering insulin at a basal insulin delivery rate and delivering a bolus insulin dose to a user using the infusion pump of the infusion unit. In such embodiments, the method also includes actuating, via a drive unit of the medical device, an insulin pump of the medical device to deliver insulin to the user at the basal insulin delivery rate, and actuating, via the drive unit, the insulin pump to deliver the selected bolus insulin dose to the user.

In some embodiments, any of the methods described herein can include determining a count of the button activations by the user during a selection time period, where the selection time period starts when the button is first activated, based on the count of the button activations by the user, select one of the plurality of preset bolus insulin doses.

In some embodiments of any of the methods described herein, confirmation of the selection of the preset bolus insulin dose can be via receipt of a user selection of a second button of the control interface.

In some embodiments of any of the methods described herein, the plurality of preset bolus insulin doses includes a set of main preset bolus insulin doses and a set of correction preset bolus insulin doses, where each correction preset bolus insulin dose is smaller than all of the main preset insulin doses.

In some embodiments of any of the methods described herein, the method can further include providing information identifying the selected preset bolus insulin dose based on one or more of a vibration or a sound generated via the control interface prior to confirmation of the selected preset bolus insulin dose.

In some embodiments of any of the methods described herein, the method can include delivering the basal insulin to the user at the basal insulin infusion rate using the insulin pump based on instructions from the controller. In some embodiments of any of the method described herein. The controller can execute instructions for determining micro-bolus insulin doses and a frequency for administration of the micro-bolus insulin doses to the user to achieve the basal insulin infusion rate and cause the insulin pump to deliver the micro-bolus insulin doses at the determined frequency to the user.

In some embodiments of the methods and devices described herein, dosing information received by the medical device or the control unit is provided by or received from a health care provider (HCP).

In some embodiments of any of the methods and devices described herein, the medical device is a wearable medical device. In some embodiments of any of the methods and devices described herein, the medical device is a portable, wearable, or hand-held medical device. In some embodiments of any of the methods and devices described herein, the medical device is portable, wearable, or hand-held and at least a portion of the medical device is implanted in the user or implantable in a user.

Some embodiments provide a non-transitory computer-readable storage medium or device configured to store instructions executable by a controller or one or more processors for implementing any of the methods described herein.

Other objects and features will become apparent from the following detailed description considered in conjunction with the accompanying drawings. It is to be understood, however, that the drawings are designed as an illustration only and not as a definition of the limits of the invention.

BRIEF DESCRIPTION OF THE DRAWINGS

FIG. 3 is a flowchart of an exemplary method that can be programmatically implemented according to an embodiment.

DESCRIPTION OF EXEMPLARY EMBODIMENTS

Figure 1:
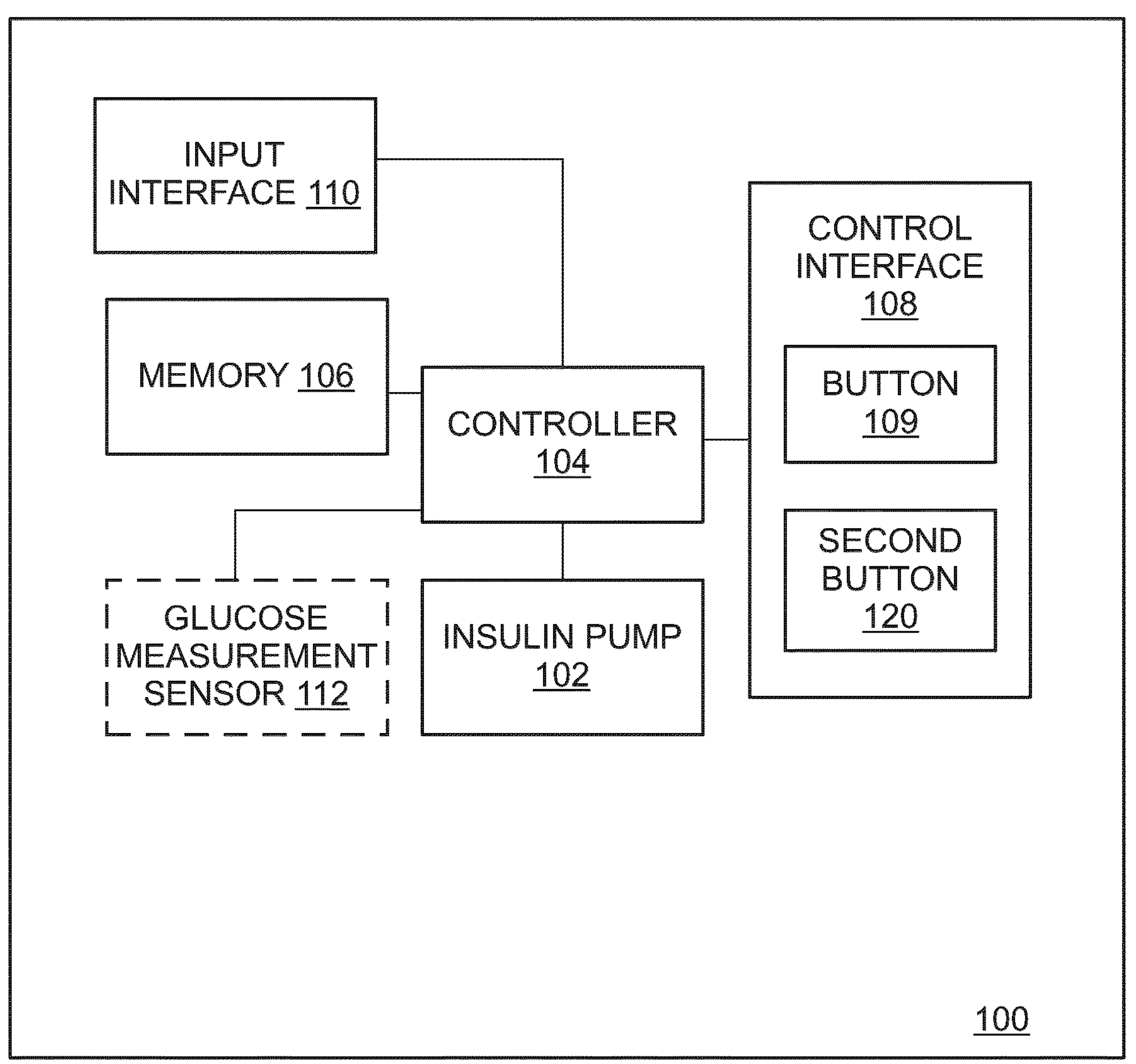
FIG. 1 is a block diagram of an exemplary medical device according to an embodiment.

Some exemplary embodiments of the present disclosure are directed to a medical device for administering daily basal insulin to a user of the medical device (e.g., a patient) and enabling easy and simple user selection of one of a plurality of preset bolus insulin doses, which are based on a determined total daily bolus insulin dose. Some exemplary embodiments of the present disclosure include methods for determining and delivering basal insulin and bolus insulin to a user of the medical device (e.g., a patient). Some methods and devices employ a simplified control interface for selection of a bolus insulin dose from among a group of preset bolus insulin doses that are determined by the device based on received dosing information (e.g., based on dosing information received from a HCP for the user). In some embodiments, the group of preset bolus insulin doses includes a set of main doses corresponding to meals with various amounts of carbohydrates and a set of smaller correction doses. In some embodiments, user selection of one of the predetermined bolus insulin doses is via a button of the medical device. In some embodiments, user selection of one of the preset bolus insulin doses is based on a number of times that the user pushes the button. In some embodiments, the medical device is configured to provide information regarding the selected preset bolus insulin doses, e.g., via a vibration of the medical device or a sound made by the medical device. In some embodiments, the medical device is configured to receive an input from the user confirming the selected preset bolus insulin dose. In some embodiments, the input confirming the selected preset bolus insulin dose is via a second button of the medical device. In some embodiments, the medical device does not include a graphical user interface. In some embodiments, the control interface for use by the user does not include a screen or a graphical display.

In some embodiments, the medical device is configured to reduce complexity and difficulty for a user to select a bolus insulin dose, through use of the preset bolus insulin doses and through use of a simplified control interface as compared with some other conventional medical devices. For example, having a single button for selecting a dose of bolus insulin from a limited number of preset insulin doses decreases the complexity and time required for the user to input or set a bolus dose as compared with some conventional devices, which may increase the ease of use of the device and decrease error associated with some user control interfaces. Many conventional medical devices are trending toward increased complexity in control interfaces to include more and more options and controls. The reduction in control interface options on a medical device in some embodiments as compared with some conventional medical devices is counterintuitive, but can result in increased adoption of bolus dose therapy and increased compliance with, and thus efficacy of, bolus dose therapy.

In some embodiments, the medical device includes a button that may be actuated (e.g., pressed or touched) multiple times to select a preset bolus insulin dose from a plurality of preset insulin doses. In some embodiments, doses in the plurality of preset bolus insulin doses are determined by the medical device as different fractions of a total daily bolus insulin dose for the user. In some embodiments the total daily bolus insulin dose of the user is provided to the medical device by a health care provider and/or programmed into the medical device by a party other than the user. The plurality of doses may not be linearly increasing. For example, in some embodiments, the plurality of preset insulin bolus doses may be $1/10$, $1/5$, $1/3$ and $1/2$ of the total daily bolus insulin dose to correspond to characterization of meals and smaller corrections.

Further, in embodiments having a second button for confirmation of the dose, the second button may reduce errors associated with using the same input mechanism for inputting the dose and confirming the dose. Other embodiments may employ the button used to select the preset bolus insulin dose to confirm the selected preset bolus insulin dose (e.g., by pressing and holding or touching and holding the button). Other embodiments may employ a different mechanism for receiving second input to confirm the selected preset bolus insulin dose. Thus, the second button is optional.

In some embodiments, the user does not need to provide any input or information regarding calories, carbohydrates, glycemic index, or blood glucose measurement prior to selection of the present bolus insulin dose using the button.

In some embodiments, the medical device can reduce complexity of interaction for the user, because it can administer the bolus dose regimen without requiring a blood glucose measurement and without requiring the user to input a blood glucose measurement. In some embodiments, the medical device receives a user input corresponding to a simplified characterization of a meal or a physical activity, which corresponds to one of the preset bolus insulin doses. For example, the medical device may receive three presses of the button to indicate a small meal, four presses of the button to indicate a medium calorie meal, or five presses of the button to indicate a large meal. The preset bolus insulin doses may also include smaller correction doses. For example, in some embodiments the user pressing the button once selects the smallest correction dose, and the user pressing the button twice selects a larger correction dose. Thus, in some embodiments, the medical device allows for a simpler method of accounting for the meals instead of carb counting and provides for easy selection of smaller correction boluses. This simplification of the interaction with the user has a surprising and beneficial effect on medical compliance, and a success rate of bolus dose therapy, while reducing human error in user selection of doses.

In some embodiments, after the medical device receives the information about the characterization of the meal, such as through the number of times a button was pressed, the medical device can provide an indication of the selection via vibration, sound and/or a visual indication. For example, in some embodiments, the medical device may vibrate four times if the button was pressed four times to alert the user that the fourth preset bolus insulin dose was selected. This indication of the selection via vibration, sound and/or a visual indication may be important in some embodiments because the simplified control interface of the medical device may not include a screen or a graphical display. In some embodiments, after the indication of the selection, the medical device can require the user to press the button used for selection again to confirm the selection before administering the selected bolus dose. In some embodiments, the input mechanism for confirming the dose is different than the button using for selecting the dose. For example, in some embodiments, the medical device includes a second button that the user activates (e.g., presses or touches) confirming the selection of a dose before administering the dose. This confirmation process may reduce error in dose selection and administration.

FIG. 1 is a block diagram of a medical device 100 (hereinafter "device 100") in accordance with some embodiments. The medical device 100 includes an insulin pump 102 configured to deliver insulin to a user (e.g., a patient), a control interface 108 including a button 109 (e.g., a bolus button) configured to select one of a plurality of preset bolus insulin doses based on input from a user, and a controller 104 configured to execute machine-readable instructions stored in a memory 106. In some embodiments, the control interface 108 includes a second button 120 for confirming the selection of a preset bolus insulin dose. In other embodiments, the confirmation of the selection may also be via the button 109.

In some embodiments, the preset bolus insulin doses are determined by the medical device based, at least in part, on received dosing information regarding the user (e.g., information received from a health care provider) for determining a total daily insulin dose and a total daily bolus insulin dose for the user. In some embodiments, doses in the plurality of preset bolus insulin doses are determined as fractions of the total daily bolus insulin dose. In some embodiments, the preset bolus insulin doses in the plurality of bolus insulin doses are not linearly increasing. In some embodiments, the preset bolus insulin doses correspond to meals having different amounts of carbohydrates (e.g., large, medium, and small) and smaller corrective doses enabling a user to simply and easily select a preset bolus insulin dose corresponding to a meal or select a smaller corrective bolus insulin dose.

In some embodiments, the medical device 100 includes a glucose measurement sensor 112 configured to measure the blood glucose of the user. In other embodiments, no glucose measurement sensor 112 is included in the medical device, which is why the glucose measurement sensor 112 is indicated in the figures by a box having a dashed line.

Examples of insulin pumps 102 include, but are not limited to, patch pumps that are worn by a user and implanted devices that deliver a dose of insulin to the bloodstream. In some embodiments, the insulin pump 102 is configured to deliver short-acting insulin. In some embodiments, the insulin pump 102 is configured to deliver short-acting and/or long-acting insulin.

In some embodiments, the button 109 and/or the second button 120 is a mechanical switch or an electromechanical switch that generates a signal when activated. In other embodiments, the button 109 and/or the second button 120 is a capacitive or inductive touch interface. In some embodiments, a number of button activations by the user during a selection time period determines which of the plurality of preset bolus insulin doses is selected. For example, pressing the button 108 five times would select the fifth preset bolus insulin does. In some embodiments, the number of preset bolus insulin doses is five or less than five. In some embodiments, the number of preset bolus insulin doses is six or less than six. In some embodiments, a number of activations of the button 109 to select any preset bolus insulin dose is less than six. In some embodiments, a number of activations of the button 109 to select any preset bolus insulin dose is less than seven. Limiting the number of preset bolus insulin doses simplifies the selection process for the user.

In some embodiments, the control interface 108 is also configured to provide information to the user indicating the selected preset bolus insulin dose. In some embodiments, the information is provided via a vibration of the medical device. In some embodiments, the information is provided via sound generated by the medical device.

In some embodiments, the controller 104 may receive a second input from the control interface 108 confirming the selected preset bolus insulin dose. For example, in some embodiments, the control interface 108 includes a second button 120, and after selecting a preset bolus insulin dose using the button 108 (e.g., the bolus button), the user activates the second button 120 (e.g., by pressing or touching the second button) providing the second input to confirm the selected preset bolus insulin dose. However, some other embodiments of the medical device do not include a second button for confirmation. For example, in some embodiments, the button 108 used for selection of the preset bolus insulin dose may also be used for second input to confirm the selected preset bolus insulin dose (e.g., pressing and holding or touching and holding the button 108 for at least some period of time may be used to confirm the selected preset bolus insulin dose). In some embodiments, the second input confirming the selected preset bolus insulin dose is received after the medical device provides information to the user indicating the selected preset bolus insulin dose (e.g., via one or more of vibration, sound, or a visual indicator).

In some embodiments, the control interface 108 for use by the user in selecting and confirming a preset bolus insulin dose does not include a graphical user interface. This can be advantageous for users who do not wish to use a separate device, such as a smart phone, or the like. The control and response of the device is greatly simplified. However, in some embodiments, it is possible to configure the device to communicate with a smart phone or the like while keeping the control interface 108 active.

In some embodiments, the controller 104 includes a processor, a field programmable gate array, an application-specific integrated circuit, a microcontroller, a peripheral interface controller (PIC), or the like. In some embodiments, the controller 104 interfaces with the memory 106 through a bus. Memory 106 can be any form of memory used to store instructions or data. Examples of memory 106 include, but are not limited to, solid state memory, computer readable media such as flash memory or the like.

In some embodiments, the medical device also includes an input interface for receiving the information regarding the user (e.g., from a health care provider). In some embodiments, the input interface 110 may be configured for wired communication and/or for short range wireless communication (e.g., via a BLUETOOTH connection) or for long range wireless communication (e.g., via cellular). In some embodiments, the input interface 110 is used to receive dosage information to customize device for the user. In some embodiments, the input interface 110 is an input/output interface enabling two way communication (e.g., with a heath care provider). In some embodiments, the input interface 110 can be a Universal Serial Bus interface, an IEEE 1394 interface, a wireless interface adapted to send and receive information. In examples, the input interface 110 may be configured to receive input from a health care professional to program the medical device 100.

For example, in some embodiments the medical device receives information (e.g., from an HCP) to program the medical device 100 using dosage information for the user. The medical device 100 determines a total daily basal insulin dose and a total daily bolus insulin dose for the user from the received dosage information. In some embodiments, the received information includes information regarding at least two of: a total daily insulin dose for the user, a total daily basal insulin dose for the user, a total daily bolus insulin dose for the user, and a ratio of the total daily basal insulin dose to the total daily bolus insulin dose for the user. For example, in some embodiments, the received information (e.g., from an HCP for programming the device) includes information regarding the total daily insulin dose and regarding a ratio of the total daily basal insulin dose to the total daily bolus insulin dose for the user. In some embodiments, in the received information includes at least one of: the total daily insulin dose for the user, the total daily basal insulin dose for the user, and the total daily bolus insulin dose for the user, and the device assumes that the total daily basal insulin dose is equal to the total daily bolus insulin dose.

In some embodiments, the HCP interacts with the medical device 100 using computer or a mobile device initially to program the medical device 100. In some examples, the HCP may provide information to customize the total daily insulin dose and the total daily bolus insulin dose for a user (e.g., a patient) based on a profile of the user and the like. In some embodiments, the controller 104 uses the information received from the HCP to reprogram the medical device 100 to customize the treatment for the user.

In some embodiments, the controller executes instructions stored in memory to determine a total daily basal insulin dose and a total daily bolus insulin dose for the user based on information received regarding at least two of: a total daily insulin dose for the user, a total daily basal insulin dose for the user, a total daily bolus insulin dose for the user, and a ratio of a total daily basal insulin dose to a total daily bolus insulin dose for the user. For example, the information received (e.g., from an HCP) can include the total daily insulin dose for the user and a ratio of the total daily basal insulin dose to the total daily bolus insulin, from which the total daily basal insulin dose and the total daily bolus insulin dose are determined. In an example, based on the received information for the user, the controller 104 may provide 50% of a user's daily insulin requirement via basal insulin delivery and allocate the other 50% for delivery via multiple preset bolus insulin doses the user can select using the button 109.

In some embodiments, controller 104 determines a basal insulin delivery rate based, at least in part, on the total daily basal insulin dose. In some embodiments, the controller 104 determines a size of micro-bolus insulin doses and a frequency of administration of the micro-bolus insulin doses to achieve the determined basal insulin delivery rate. The instructions may include a process for determining a number of times per hour the insulin pump 102 has to be operated and the quantity of the micro-bolus insulin dose per operation, the unit of time between micro-bolus insulin doses and the like. In some embodiments, the insulin pump 102 may operate continually to deliver a continuous basal rate of insulin to the user. The process for determining the basal insulin delivery rate may be different for different types of insulin such as short-acting insulin, long-acting insulin and the like. For example, in some embodiments, the process may determine the minutes between micro-bolus based on the following:

Minutes between micro-bolus=60 min/(TDBasal [μL]/24 h/Vol micro-bolus [μL]), where TDBasal is the total daily basal dose of insulin and micro-bolus is the volume of insulin delivered every time the insulin pump 102 is activated.

The controller 104 determines a plurality of preset bolus insulin doses, based, at least in part, on the total daily bolus insulin dose. For example, in some embodiments, the instructions include a process for determining the plurality of preset bolus insulin doses based on the total daily bolus insulin dose. A non-limiting example of such a process is included below. In an embodiment, the process divides the total daily bolus insulin dose into a plurality of preset bolus insulin doses. In some embodiments, the plurality of preset bolus insulin doses can be five preset bolus insulin doses, such as 5% of the total daily bolus insulin dose (TDBolus) for minor correction, 12.5% of the TDBolus for major correction, 20% of the TDBolus for a small meal (small amount of carbohydrates (CHO)), 35% of the TDBolus for a medium meal (medium amount of CHO) and 50% of the TDBolus for a large meal (large amount of CHO). Other numbers of preset bolus insulin doses and other divisions of the total daily bolus insulin does also fall within the scope of the present disclosure. Table 1 below includes a non-limiting example split of the total daily bolus insulin dose and calculated estimated impact on blood glucose level.

For Table 1, it was assumed that the total daily basal insulin dose was about equal to the total daily bolus insulin dose, and that the daily total carbohydrate intake was 240 grams. The average expected impact of an insulin dose on blood glucose was assumed to follow the 1600 rule below $$dBG = 1600/DIR,$$

where dBG is the blood glucose decline in mg/ml and DIR is the daily insulin requirement. Some people have higher insulin or lower insulin sensitivity, which may not be accurately characterized by the "1600 rule" equation above.

In this example, because the total daily basal insulin dose and the total daily bolus insulin dose were about equal, the respective preset sizes also reflect a similar proportion of the basal rate.

In an example, the controller 104 may receive a signal from the bolus button 108. For example, the user may characterize a meal after the meal, characterize the correction based on the exercise before the meal or after the meal, characterize exercise between this meal and the previous meal and the like, by activating the bolus button 108. The controller 104 may use the number of times the bolus button 108 is activated within a predetermined period of time to characterize the meal, exercise or both. In an example, the predetermined period of time may be a few seconds after the bolus button 108 is activated for the first time. The controller 104 may determine the number of times the bolus button 108 was pressed to select a bolus insulin dose from the set of bolus insulin presets to be administered. For example, controller 104 may determine that the bolus insulin dose to be administered after four activations of the bolus button is a bolus insulin dose for a fourth preset bolus insulin dose, which for the example in Table 1 is a medium meal. In some embodiments, the controller 104 may receive a signal from a second button 120 to confirm a preset bolus insulin dose selected using the bolus button 108. The controller 104 may activate the insulin pump 102 to deliver the selected bolus insulin dose, which in some embodiments is a selected and confirmed preset bolus insulin dose, to the user.

In an example, the button 108 may be activated to characterize a meal.

The use of the bolus button 108 allows the controller 104 to receive information about a meal of the user, for selection of a preset bolus insulin dose without requiring the user to categorize the meals using complicated methodologies such as carb counting, individual dose dialing or setting and the like.

In some embodiments, the frequency of activation of the bolus button 108 is based on a characterization of a meal. For example, as described above, a user may activate the bolus button 108 four times to indicate a moderate meal for the embodiment of preset bolus insulin doses shown in Table 1. Similarly, the frequency of activation of the bolus button 108 may be based on the characterization of the physical activity of the user, for example, the physical activity of the user before a meal, between a previous meal and the current meal and the like. Similarly, the frequency of activation of the bolus button 108 may be based on a characterization of physical activity and a previous meal of the user.

In some embodiments, the glucose measurement sensor 112 can interface with the controller 104 to determine the blood glucose levels of a user before a bolus insulin dose is administered to the user.

In some embodiments, the medical device 100 is configured to receive at least one reservoir holding insulin. In some embodiments, the medical device 100 is configured to receive more than one reservoir, each holding a different type of insulin.

Figure 2A:
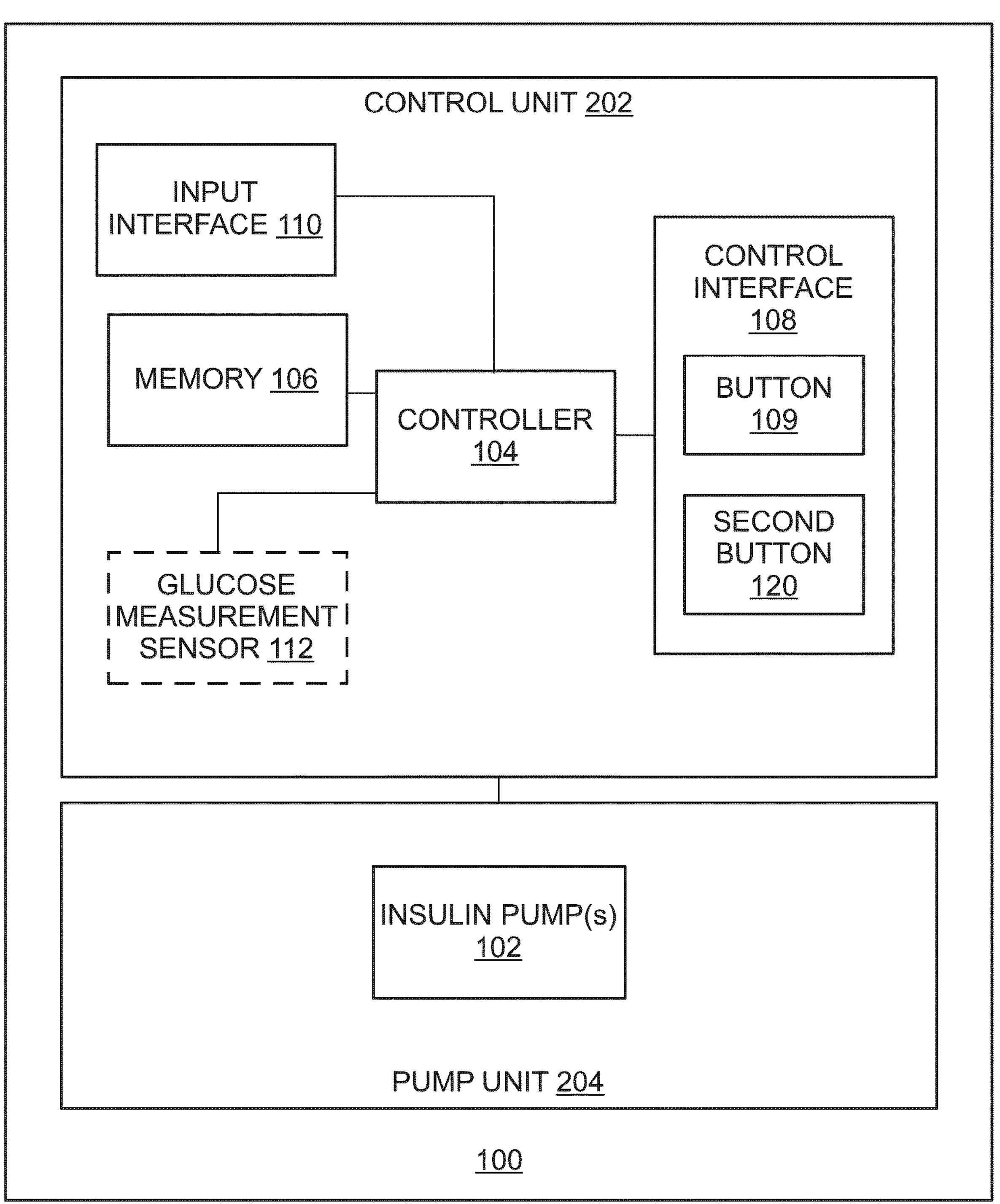
FIG. 2A is a block diagram of an exemplary medical device including a control unit and a pump unit according to an embodiment.
Figure 2B:
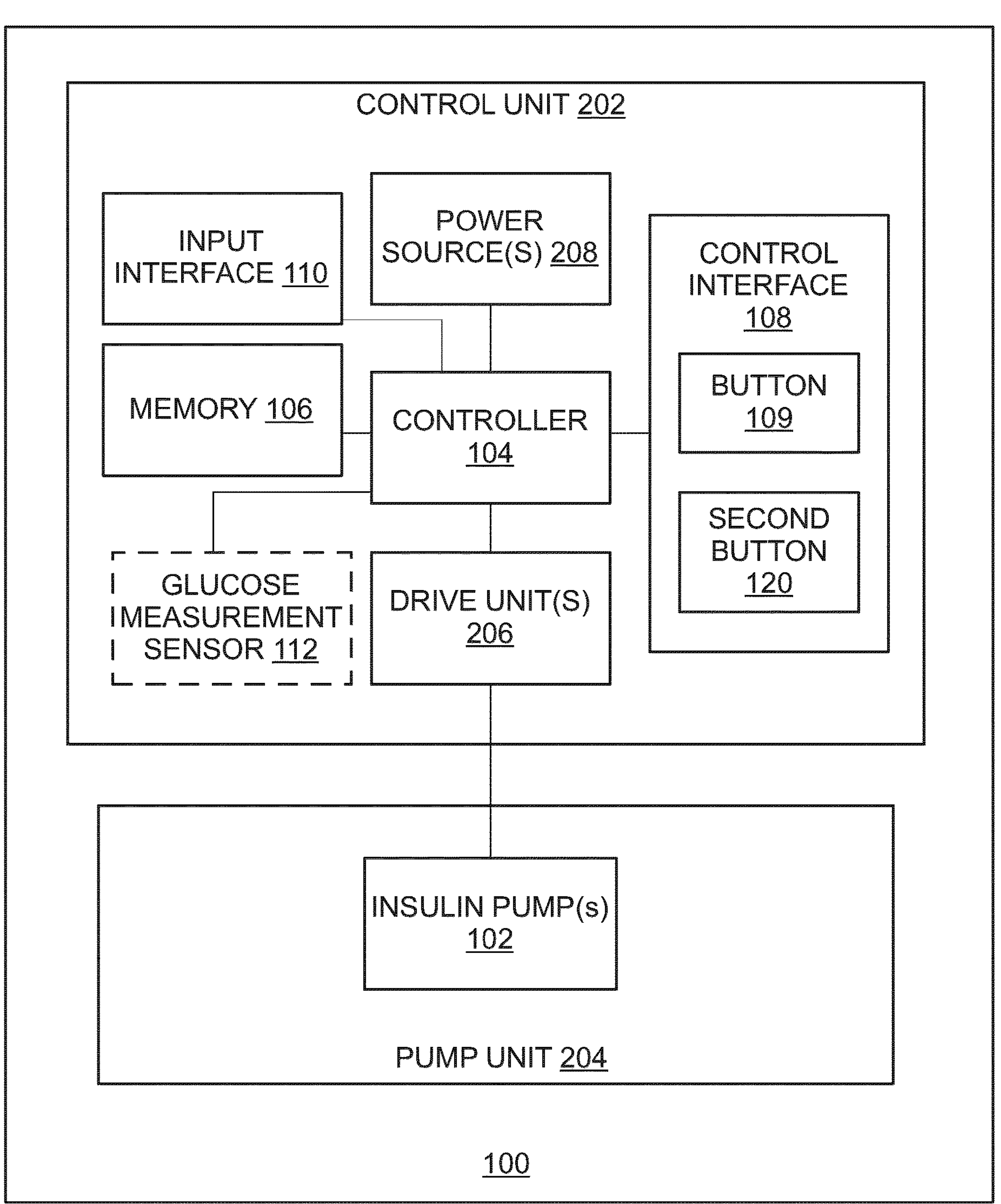
FIG. 2B is a block diagram of an exemplary medical device including a control unit that includes a drive unit according to an embodiment.

FIGS. 2A and 2B schematically depict an exemplary medical device 100, in accordance with some embodiments. The exemplary medical device 100 may include a control unit 202, and a pump unit 204. In some embodiments, the control unit 202 includes the controller 104, the memory 106, and a control interface 108 including the button 109 (e.g., a bolus button) used to select the preset bolus insulin dose from a plurality of preset bolus insulin doses. As described above, in some embodiments, the control interface 108 also provides information to the user indicating the selected preset bolus insulin dose (e.g., via one or more of vibration, sound, or a visual indicator). In some embodiments, the control interface 108 also includes a second button 120 used for receiving second input to confirm the selected preset bolus insulin dose. For example, in some embodiments, the user activates (e.g., presses or touches) the button 108 one or more times to select the present bolus insulin dose, the medical device provides an indication of the selected preset bolus insulin dose (e.g., via one or more of vibration, sound or a visual indicator), and then the user activates (e.g., presses or touches) the second button 120 to confirm the selected preset bolus insulin dose. In some embodiments, the button 108 or some other element of the control interface 108 is used to confirm the selected dose, e.g., pressing and holding the button 108 may be used to confirm the selected dose. In some embodiments, the second button 120 is used as a start/stop button for delivering insulin.

In embodiments requiring confirmation, the selected preset bolus insulin dose will only be delivered to the user if the confirming second input is received. In some embodiments, the second input for confirmation must be received within a preset confirmation time after selection of the preset bolus insulin dose.

In some embodiments, the control unit 202 includes a glucose measurement sensor 112. However, in other embodiments, no glucose measurement sensor is included, which is why the glucose measurement sensor 112 is indicated by a dashed line in FIGS. 2A and 2B.

The pump unit 204 includes at least one insulin pump 102, which may be a patch pump, an implantable pump or any other pump employed for delivering insulin to a user. In some embodiments in which more than one different type of insulin may be delivered to a user, the pump unit 204 may include more than one pump, with each pump dispensing a different type of insulin.

In some embodiments, the control unit 202 further includes at least one power source 208 (e.g., a battery) and at least one drive unit 206 for mechanically actuating the at least one insulin pump 102 (see FIG. 2B). In other embodiments, the at least one drive unit 206 may not be included in the control unit.

In some embodiments, the control unit 202 is coupled to or couplable to the pump unit 204 by the user. In some embodiments, the control unit 202 and/or the pump unit 204 include a coupling for coupling the units together. In other embodiments, the control unit 202 and the pump unit 204 are not intended to be separable by the user or are not separable by the user without damaging the medical device or rendering the medical device nonfunctional.

As described above, the controller 104 may determine a basal insulin delivery rate based at least in part on the total daily basal insulin dose. The controller 104 may provide a signal or instructions to the drive unit 206 causing the drive unit to mechanically actuate the insulin pump 102 of the pump unit 204 to deliver insulin, via the insulin pump 102, to the user at the basal insulin delivery rate. After selection of the preset basal insulin dose, the controller 104 may provide a signal or instructions to the drive unit 206 causing the drive unit to mechanically actuate the insulin pump 102 of the pump unit 204 to deliver the selected bolus insulin dose, via the insulin pump 102, to the user.

FIG. 3 shows a flowchart 300 of an exemplary method for determining a basal insulin delivery rate and a bolus insulin dose for a user. A total daily basal insulin dose and a total daily basal insulin dose are determined by a controller 104 based on dosing information for a user received via an input interface 109 of a control unit 202 (Step 302). In some embodiments, the dosing information includes at least two of the following: (i) a total daily insulin dose for the user, (ii) a total daily basal insulin dose for the user, (iii) a total daily bolus insulin dose for the user, and (iv) a ratio of a total daily basal insulin dose to a total daily bolus insulin dose for the user. For example, in some embodiments, the dosing information includes the total daily insulin dose for the user and the ratio of a total daily basal insulin dose to a total daily bolus insulin dose for the user. In some embodiments, the medical device is configured based on the assumption that the total daily basal insulin dose is the same as the total daily bolus insulin dose, in which case, the information received may include only one or more of the following: (i) a total daily insulin dose for the user, (ii) a total daily basal insulin dose for the user, and (iii) a total daily bolus insulin dose for the user.

The controller 104 of the control unit 202 determines a plurality of preset bolus insulin doses for selection using a button 109 of a control interface 108 of the control unit 202 based, at least in part, on the determined total daily bolus insulin dose for the user (Step 304).

The controller 104 of the control unit 202 determines a basal insulin delivery rate based, at least in part, on the determined total daily basal insulin dose (Step 306).

In some embodiments where the method is also a method of delivering basal insulin and delivering bolus insulin, the method also includes the controller 104 actuating, via the drive unit 206, the insulin pump 102 of the pump unit 204 to deliver insulin, via the insulin pump 102, to the user at the basal insulin delivery rate (Step 308).

The controller 104 of the control unit 202 receives a first input from the user via the button 109 of the control interface 109 of the control unit, the first input selecting one of the plurality of preset bolus insulin doses (Step 310).

In some embodiments, the controller provides an indication (e.g., a vibration, an audio, and/or a visual indication) of the selected preset bolus insulin dose to the user via the control interface 202 (Step 311).

In some embodiments, the controller 104 receives a second input from the user via the control interface 108 confirming the selected preset bolus insulin dose within a confirmation time period after selection of the preset bolus insulin dose (Step 312). For example the second input may be from the user pressing or touching the second button 120 to confirm the selected preset bolus insulin dose after the medical device provides the indication to the user of the selected preset bolus insulin dose.

In some embodiments where the method is also a method of delivering basal insulin and delivering bolus insulin, the method further includes actuating, via the drive unit 206, the insulin pump 102 to deliver the selected bolus insulin dose to the user (Step 314). In FIG. 3, steps that may not be performed in some embodiments are indicated with dashed lines.

Figure 4:
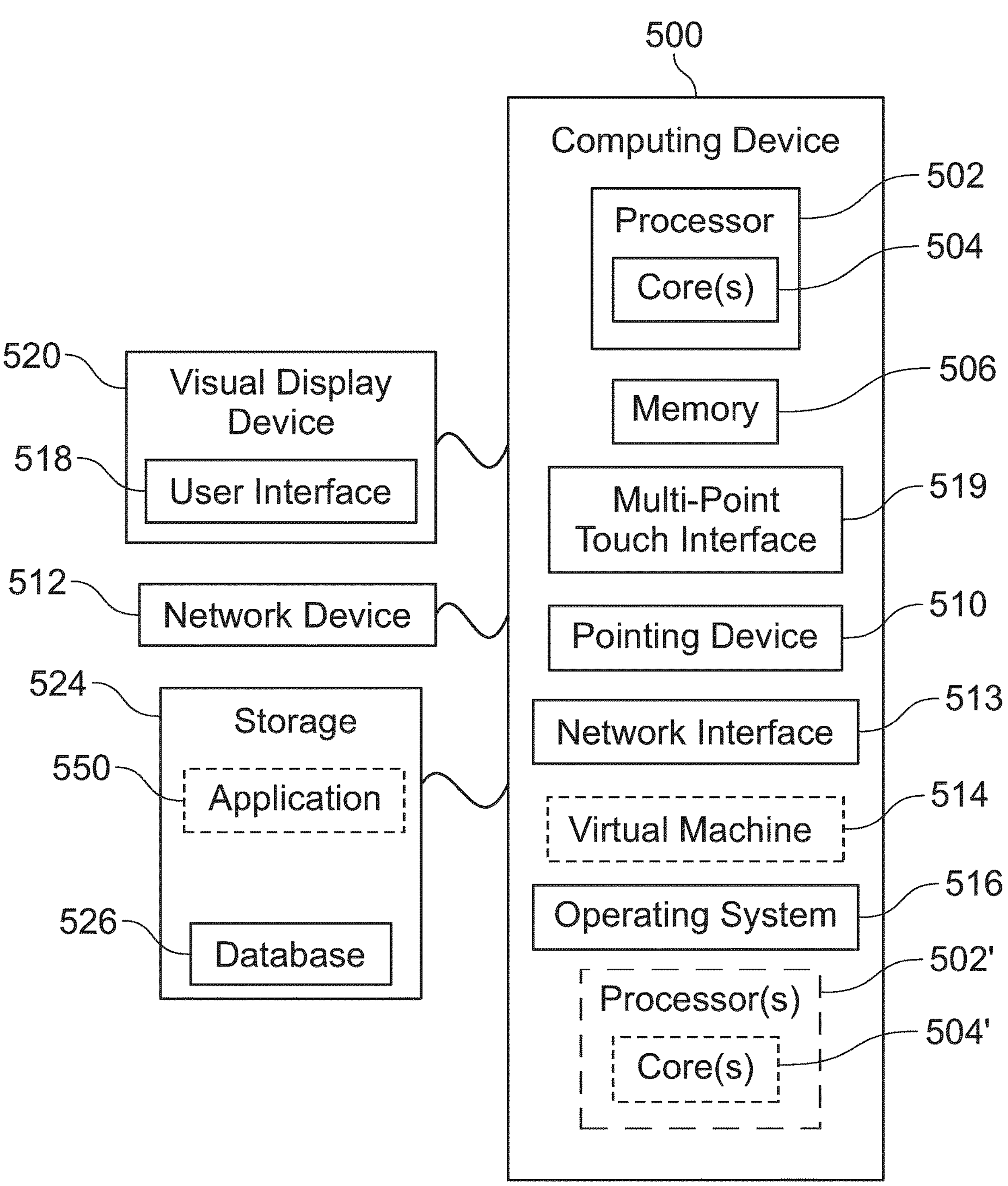
FIG. 4 is a block diagram of an exemplary computing device for implementing the methods according to an embodiment.

FIG. 4 is a block diagram of an exemplary computing device 500 that may be used to implement exemplary embodiments that the HCP may use to program the medical device 100. The computing device 500 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives), and the like. For example, memory 506 included in the computing device 500 may store computer-readable and computer-executable instructions or software for implementing exemplary embodiments of the medical device 100. The computing device 500 also includes configurable and/or programmable processor 502 and associated core 504, and optionally, one or more additional configurable and/or programmable processor(s) 502' and associated core(s) 504' (for example, in the case of computer systems having multiple processors/cores), for executing computer-readable and computer-executable instructions or software stored in the memory 506 and other programs for controlling system hardware. Processor 502 and processor(s) 502' may each be a single core processor or multiple core (504 and 504') processor.

Virtualization may be employed in the computing device 500 so that infrastructure and resources in the computing device may be shared dynamically. A virtual machine 514 may be provided to handle a process running on multiple processors so that the process appears to be using only one computing resource rather than multiple computing resources. Multiple virtual machines may also be used with one processor.

Memory 506 may include a computer system memory or random access memory, such as DRAM, SRAM, EDO RAM, and the like. Memory 506 may include other types of memory as well, or combinations thereof.

A user (e.g., a user associated with the HCP) may interact with the computing device 500 through a visual display device 518, such as a computer monitor, which may display one or more user interfaces 520 that may be provided in accordance with exemplary embodiments. The computing device 500 may include other I/O devices for receiving input from a user, for example, a keyboard or any suitable multi-point touch interface 519, a pointing device 510 (e.g., a mouse). The keyboard 508 and the pointing device 510 may be coupled to the visual display device 520. The computing device 500 may include other suitable conventional I/O peripherals.

The computing device 500 may also include one or more storage devices 524, such as a hard-drive, CD-ROM, or other computer readable media, for storing data and computer-readable instructions and/or software that implement exemplary embodiments of a computing device the HCP may use to interact with the medical device 100 described herein. Exemplary storage device 524 may also store instructions and/or software that implements an application 550 that may also store one or more databases for storing any suitable information required to program the medical device 100 according to exemplary embodiments. For example, exemplary storage device 524 can store one or more databases 526 for storing information, such as information corresponding to one or more commands, operations, passcodes, user identifiers, and/or any other information to be used to program the embodiments of the medical device 100. The databases may be updated by manually or automatically at any suitable time to add, delete, and/or update one or more items in the databases.

The computing device 500 can include a network interface 512 configured and/or programmed to interface via one or more network devices 513 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 512 may include a built-in network adapter, network interface card, PCMCIA network card, card bus network adapter, wireless network adapter, USB network adapter, modem or any other device suitable for interfacing the computing device 500 to any type of network capable of communication and performing the operations described herein. Moreover, the computing device 500 may be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The computing device 500 may run any operating system 516, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing device and performing the operations described herein. In exemplary embodiments, the operating system 516 may be run in native mode or emulated mode. In an exemplary embodiment, the operating system 516 may be run on one or more cloud machine instances.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba@); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

In describing exemplary embodiments, specific terminology is used for the sake of clarity. For purposes of description, each specific term is intended to at least include all technical and functional equivalents that operate in a similar manner to accomplish a similar purpose.

Additionally, in some instances where a particular exemplary embodiment includes a plurality of system elements, device components or method steps, those elements, components or steps may be replaced with a single element, component or step. Likewise, a single element, component or step may be replaced with a plurality of elements, components or steps that serve the same purpose. Moreover, while exemplary embodiments have been shown and described with references to particular embodiments thereof, those of ordinary skill in the art will understand that various substitutions and alterations in form and detail may be made therein without departing from the scope of the invention. Further, still, other embodiments, functions, and advantages are also within the scope of the invention.

Exemplary flowcharts are provided herein for illustrative purposes and are non-limiting examples of methods. One of ordinary skill in the art will recognize that exemplary methods may include more or fewer steps than those illustrated in the exemplary flowcharts and that the steps in the exemplary flowcharts may be performed in a different order than the order shown in the illustrative flowcharts.

Listing of Reference Numbers

| | |
|---|---|
| 100 | medical device |
| 102 | insulin pump |
| 104 | controller |
| 106 | memory |
| 108 | control interface |
| 109 | button |
| 110 | input interface |
| 112 | glucose measurement sensor |
| 120 | second button |
| 202 | control unit |
| 204 | pump unit |
| 206 | drive unit |
| 208 | power source |
| 300-314 | method |
| 500 | computing device |
| 502 | processor |
| 502' | virtual processor |
| 504 | core |
| 504' | virtual core |
| 506 | memory |
| 510 | pointing device |
| 512 | network interface |
| 513 | network interface device |
| 514 | virtual machine |
| 516 | operating system |
| 518 | user interface |
| 519 | multi-point touch interface |
| 520 | visual display device |
| 524 | storage |
| 526 | database |
| 550 | application |

TABLE 1

| | | | Total daily bolus insulin dose | | | | | | |
|---|---|---|---|---|---|---|---|---|---|
| | | | u/d CHO [g] | 20 | 24 | 28 | 35 | 45 | 60 |
| | | | | Bolus size [units] dBG [mg/dl] | | | | | |
| Meals | | big meal | 120 | | | | | | |
| | | 3/6 | | 10.0 | 12.0 | 14.0 | 17.5 | 22.5 | 30.0 |
| | | (0.5) | | | | 400 | | | |
| | | medium meal | 80 | | | | | | |
| | | 2/6 | | 6.7 | 8.0 | 9.3 | 11.7 | 15.0 | 20.0 |
| | | (0.333) | | | | 267 | | | |
| | | medium-small meal/large + BG correction | 48 | | | | | | |
| | | 1/5 | | 4.0 | 4.8 | 5.6 | 7.0 | 9.0 | 12.0 |
| | | (0.200) | | | | 160 | | | |
| | BG corrections | small meal/large BG correction | 30 | | | | | | |
| | | 1/8 | | 2.5 | 3.0 | 3.5 | 4.4 | 5.6 | 7.5 |
| | | (0.125) | | | | 100 | | | |
| | | small BG correction | 12 | | | | | | |
| | | 1/20 | | 1.0 | 1.2 | 1.4 | 1.8 | 2.3 | 3.0 |
| | | (0.050) | | | | 40 | | | |

The invention claimed is:

1. A device comprising:

an insulin pump configured to deliver insulin;

a control interface including a button configured to select one of a plurality of preset bolus insulin doses based on an input from a user, the plurality of preset bolus insulin doses determined by a controller; and the controller configured for executing instructions stored in a memory to:

determine a total daily basal insulin requirement and a total daily bolus insulin requirement for the user based on received dosing information for the user regarding at least two of: a total daily insulin requirement for the user, a total daily basal insulin requirement for the user, a total daily bolus insulin requirement for the user, and a ratio of the total daily basal insulin requirement to the total daily bolus insulin requirement for the user;

determine the plurality of preset bolus insulin doses based, at least in part, on the total daily bolus insulin requirement;

determine a basal insulin delivery rate based, at least in part, on the total daily basal insulin requirement;

deliver insulin, via the insulin pump, to the user at the basal insulin delivery rate;

receive a first input from the user via the button selecting one of the plurality of preset bolus insulin doses; and deliver the selected bolus insulin dose, via the insulin pump, to the user.

2. The device of claim 1, wherein the controller is further configured to:

determine a count of activations of the button by the user during a selection time period, wherein the selection time period starts when the button is first activated; and based on the count of the button activations by the user during the selection time period, select one of the plurality of preset bolus insulin doses.

3. The device of claim 2, wherein the controller is further configured to select a preset bolus insulin dose amongst the plurality of preset bolus insulin doses based on the count of the button activations by the user during the selection time period, where an increase in the count of the button activations by the user during the selection time period results in selection of a preset bolus insulin dose with a progressively larger quantity of insulin.

4. The device of claim 1, wherein the controller is further configured to:

provide information indicating the selected preset bolus insulin dose to the user via the control interface; and receive a second input from the user via the control interface confirming the selected preset bolus insulin dose within a confirmation time period after selection of the preset bolus insulin dose.

5. The device of claim 4, wherein the control interface further comprises a second button configured to confirm the selection of the preset bolus insulin dose.

6. The device of claim 4, wherein the controller is further configured to provide the information indicating the selected preset bolus insulin dose to the user based on one or more of a vibration or a sound generated via the control interface.

7. The device of claim 1, wherein the plurality of preset bolus insulin doses includes a set of main preset bolus insulin doses and a set of correction preset bolus insulin doses, and wherein each correction preset bolus insulin dose is smaller than all of the main preset insulin doses.

8. The device of claim 1, wherein the controller is further configured to:

determine micro-bolus insulin doses and a frequency for administration of the micro-bolus insulin doses to the user to achieve the basal insulin delivery rate; and deliver to the user, via the insulin pump, the determined micro-bolus insulin doses at the determined frequency.

9. The device of claim 1, wherein the controller is further configured to:

receive, via an input interface, the dosing information for the user for determining the total daily basal insulin requirement and the total daily bolus insulin requirement; and store the received information in the memory.

10. The device of claim 1, further comprising:

a control unit that includes the controller and the control interface; and a pump unit that includes the insulin pump.

11. The device of claim 1, further comprising a blood glucose measuring unit configured to determine a blood glucose value that corresponds to a current blood glucose level of the user.

12. A control unit for a medical device, the control unit comprising:

a control interface including a button configured to select one of a plurality of preset bolus insulin doses based on an input from a user, the plurality of preset bolus insulin doses determined by a controller; and the controller configured for executing instructions stored in a memory to:

determine a total daily basal insulin requirement and a total daily bolus insulin requirement for the user based on received dosing information for the user regarding at least two of: a total daily insulin requirement for the user, a total daily basal insulin requirement for the user, a total daily bolus insulin requirement for the user, and a ratio of the total daily basal insulin requirement to the total daily bolus insulin requirement for the user;

determine the plurality of preset bolus insulin doses based, at least in part, on the total daily bolus insulin requirement;

determine a basal insulin delivery rate based, at least in part, on the total daily basal insulin requirement;

actuate, via a drive unit, an insulin pump of a pump unit to deliver insulin to the user at the basal insulin delivery rate;

receive a first input from the user via the button selecting one of the plurality of preset bolus insulin doses; and actuate, via the drive unit, the insulin pump of the pump unit to deliver the selected bolus insulin dose to the user.

13. The control unit of claim 12, wherein the controller is further configured to:

determine a count of activations of the button by the user during a selection time period, wherein the selection time period starts when the button is first activated; and based on the count of the button activations by the user during the selection time period, select one of the plurality of preset bolus insulin doses.

14. The control unit of claim 13, wherein the controller is further configured to select a preset bolus insulin dose amongst the plurality of preset bolus insulin doses based on the count of the button activations by the user during the selection time period, where an increase in the count of the button activations by the user during the selection time period results in selection of a preset bolus insulin dose with a progressively larger quantity of insulin.

15. A method comprising:

determining a total daily basal insulin requirement and a total daily bolus insulin requirement for a user based on dosing information for the user received via an input interface of a medical device regarding at least two of: a total daily insulin requirement for the user, a total daily basal insulin requirement for the user, a total daily bolus insulin requirement for the user, and a ratio of a total daily basal insulin requirement to a total daily bolus insulin requirement for the user;

determining, via a controller of the medical device, a plurality of preset bolus insulin doses for selection using a button of a control interface of the medical device based, at least in part, on the total daily bolus insulin requirement for the user;

determining, via the controller, a basal insulin delivery rate based, at least in part, on the total daily basal insulin requirement;

receiving a first input from the user via the button of the control interface, the first input selecting one of the plurality of preset bolus insulin doses;

providing information indicating the selected preset bolus insulin dose to the user via the control interface; and receiving a second input from the user via the control interface confirming the selected preset bolus insulin dose within a confirmation time period after selection of the preset bolus insulin dose.

16. The method of claim 15, wherein receiving the first input from the user via the button of the control interface comprises:

determining a count of activations of the button by the user during a selection time period, wherein the selection time period starts when the button is first activated; and selecting one of the plurality of preset bolus insulin doses based on the count of the button activations by the user during the selection time period, where an increase in the count of the button activations by the user during the selection time period results in selection of a preset bolus insulin dose with a progressively larger quantity of insulin.

17. The method of claim 15, wherein the plurality of preset bolus insulin doses includes a set of main preset bolus insulin doses and a set of correction preset bolus insulin doses, and wherein each correction preset bolus insulin dose is smaller than all of the main present insulin doses.

18. The method of claim 15, further comprising:

determining micro-bolus insulin doses and a frequency for administration of the micro-bolus insulin doses to the user to achieve the basal insulin delivery rate; and delivering to the user the determined micro-bolus insulin doses at the determined frequency via an insulin pump of the medical device.

19. The method of claim 15, further comprising:

actuating, via a drive unit, an insulin pump of a pump unit of the medical device to deliver insulin to the user at the basal insulin delivery rate; and actuating, via the drive unit, the insulin pump of the pump unit to deliver the selected bolus insulin dose to the user.

20. The method of claim 15, wherein providing the information indicating the selected preset bolus insulin dose to the user via the control interface comprises generating a vibration, generating a sound, or generating a vibration and a sound.

* * * * *